United States Patent [19]

Schnaar

[11] Patent Number: 5,192,508
[45] Date of Patent: Mar. 9, 1993

[54] CARBOHYDRATE CELLULAR ADHESION APPARATUS

[75] Inventor: Ronald L. Schnaar, Columbus, Md.

[73] Assignee: The Johns Hopkins University, Baltimore, Md.

[21] Appl. No.: 902,755

[22] Filed: Jun. 23, 1992

Related U.S. Application Data

[63] Continuation of Ser. No. 192,959, May 12, 1988, abandoned.

[51] Int. Cl.[5] .......................... B01L 3/08; C12M 1/18
[52] U.S. Cl. ........................................ 422/70; 422/72; 422/102; 422/104; 435/299; 435/300
[58] Field of Search ............... 422/70, 72, 102, 101, 422/104; 435/299, 300

[56] References Cited

U.S. PATENT DOCUMENTS

| | | | |
|---|---|---|---|
| 4,077,515 | 3/1978 | Shoberg | 206/456 |
| 4,314,897 | 2/1982 | Monte et al. | 422/102 X |
| 4,549,655 | 10/1985 | Forsythe, Jr. et al. | 206/456 X |
| 4,834,946 | 5/1989 | Levin | 422/101 |

*Primary Examiner*—Jill A. Johnston
*Attorney, Agent, or Firm*—Spensley Horn Jubas & Lubitz

[57] ABSTRACT

An apparatus is provided for determining binding of mammalian cells to carbohydrates on a chromatographic plate surface. The chromatogram is performed, the plate introduced into a cell adhesion chamber, and the chamber filled with an appropriate cell containing medium. After mild centrifugation to ensure cell carbohydrates interaction, non-specific adherent cells are removed by gravitational force in the opposite direction. The plate is then carefully washed without subjecting the plate to any air/liquid interface, the cells fixed and the plate analyzed.

6 Claims, 3 Drawing Sheets

CARBOHYDRATE CELLULAR ADHESION APPARATUS

This invention was made with government support under grant/contract numbers HD-14010 and HD-20527 awarded by the National Institutes of Health. The government has certain rights in this invention.

This is a continuation of application Ser. No. 07/192,959 filed on May 12, 1988, now abandoned.

INTRODUCTION

1. Technical Field

The field of this invention concerns detection of weakly binding ligands to eukaryotic cellular receptors on whole cells.

2. Background

Cell-cell recognition and adhesion may be mediated by cell surface complex carbohydrates and complementary carbohydrate receptors. A large number of naturally occurring polysaccharides exist which may serve a variety of physiological functions. The cell surface of different cells may include a number of markers involving sugars bound to lipids as the manner in which the sugars are maintained on the cell surface. In lysing cells, one will usually obtain a complex mixture of glycolipids. There is substantial interest in being able to identify a specific glycolipid with a particular interaction or physiological role for the cell.

While lipids can be separated into relatively pure fractions by a variety of means, screening for receptors with a particular cell type or mixture of cells is not easily performed. Desirably, viable cells are employed, so that one can enhance the possibility for a specific binding between the glycolipid and its receptor, as distinct from non-specific binding. By being able to determine the particular glycolipid involved with cell-cell interactions, drugs may be designed which may act in the enhancement or inhibition of the cell-cell interaction.

Relevant Literature

Brandley and Schnaar, *J. Leukocyte Biol.* (1986) 40:97-111; Roseman, *Chem. Phys. Lipids* (1970) 5:270-297; and Hakomori, *Ann. Rev. Biochem.* (1981) 50:733-764, report that cell-cell recognition and adhesion may be mediated by cell surface complex carbohydrates and complementary carbohydrate receptors. The glycosphingolipids have been demonstrated to mediate the binding of bacterial toxins (Rogers and Snyder *J. Biol. Chem.* (1981) 256:2402-2407; Tsuji, et al., *ibid* (1985) 260:8552-8558; Holmgren et al., *Infect. Immun.* (1973) 8:208-214), bacteria (Bock et al., *J. Biol. Chem.* (1985) 260:8545-8551; Hansson et al., *Anal. Biochem.* (1985) 146:158-163) and viruses (Holmgren et al., *Proc. Natl. Acad. Sci. USA* (1980) 77:1947-1950; Suzuki et al., *J. Biol. Chem.* (1985) 260:1362-1365; Hansson et al., *FEBS Lett.* (1984) 170:15-18), to cell surfaces and have been proposed as mediators of cell-cell recognition and adhesion (Hakomori, *Sci. Amer.* (1986) 254:44-53). Magnani et al., *Anal. Biochem.* (1980) 109:399-402, have reported direct TLC-binding assays for glycosphingolipids. Minor components of partially purified glycosphingolipid mixtures were shown to support the binding of particular antibodies or toxins (*Magnani et al., supra;* Fredman et al., *Arch. Biochem. Biophys.* (1984) 233:661-666; Fishman et al., *J. Biol. Chem.* (1984) 259:7983-7989. The ability of radio-labeled viruses and bacteria to bind directly to specific glycosphingolipids separated on TLC plates has been reported by Bach et al., *supra;* Hansson et al. (1985), *supra;* Hansson et al. (1984), *supra*. Swank-Hill et al., *Anal. Biochem.* (1987) 163:27-35, describe a method and apparatus for carbohydrate-specific cell adhesion directly to glycosphingolipids separated on thin-layer chromatography plates. This last reference is specifically incorporated herein by reference.

SUMMARY OF THE INVENTION

Binding of receptors on the cell surface of viable cells to chromatographically separated carbohydrates, particularly glycolipids, is achieved by contacting a chromatographic plate on which carbohydrates have been separated, where the plate is stabilized with a polymeric solution, with cells in an aqueous medium under mild gravitational forces to provide for adhesion. Non-specifically bound cells are removed by reversing the gravitational force. The plate is then manipulated without transfer through an air/liquid interface until the cells are fixed. The presence of the cells in conjunction with a particular saccharide ligand is then determined in accordance with conventional ways.

DESCRIPTION OF THE SPECIFIC EMBODIMENTS

Methods and apparatus are provided for interrelating relatively weakly binding ligands, particularly carbohydrates, such as glycolipids, with naturally occurring cell surface receptors which exist as part of the surface of viable cells. The method comprises separating a source of the ligand by thin layer chromatography (TLC), drying the chromatogram, stabilizing the chromatogram with a dilute polymeric solution in an inert medium, inserting the chromatogram into a container having a chamber where the chromatogram plate is held in a fixed position and introducing the cells into the chamber in appropriate media. The chamber is then sealed in the substantial absence of air bubbles in the chamber. The chamber is then subjected to a gravitational force in the direction of directing the cells to the surface of the plate, followed by a somewhat greater gravitational force in the opposite direction to remove non-specifically bound cells. Without passing the plate through an air/liquid interface, the plate is washed and the cells fixed. The presence of the carbohydrates may be determined by any convenient conventional manner.

The carbohydrates may be simple or complex carbohydrates having 1, usually 2 or more sugar units, which may be the same or different, or may be glycoconjugates, such as glycolipids, glycoproteins, proteoglycans, where the sugars may be further substituted, for example, acetylated, methylated, phosphorylated, etc. or unsubstituted, and hydroxyl groups may be replaced with thio, amino, etc.

Figure 3:
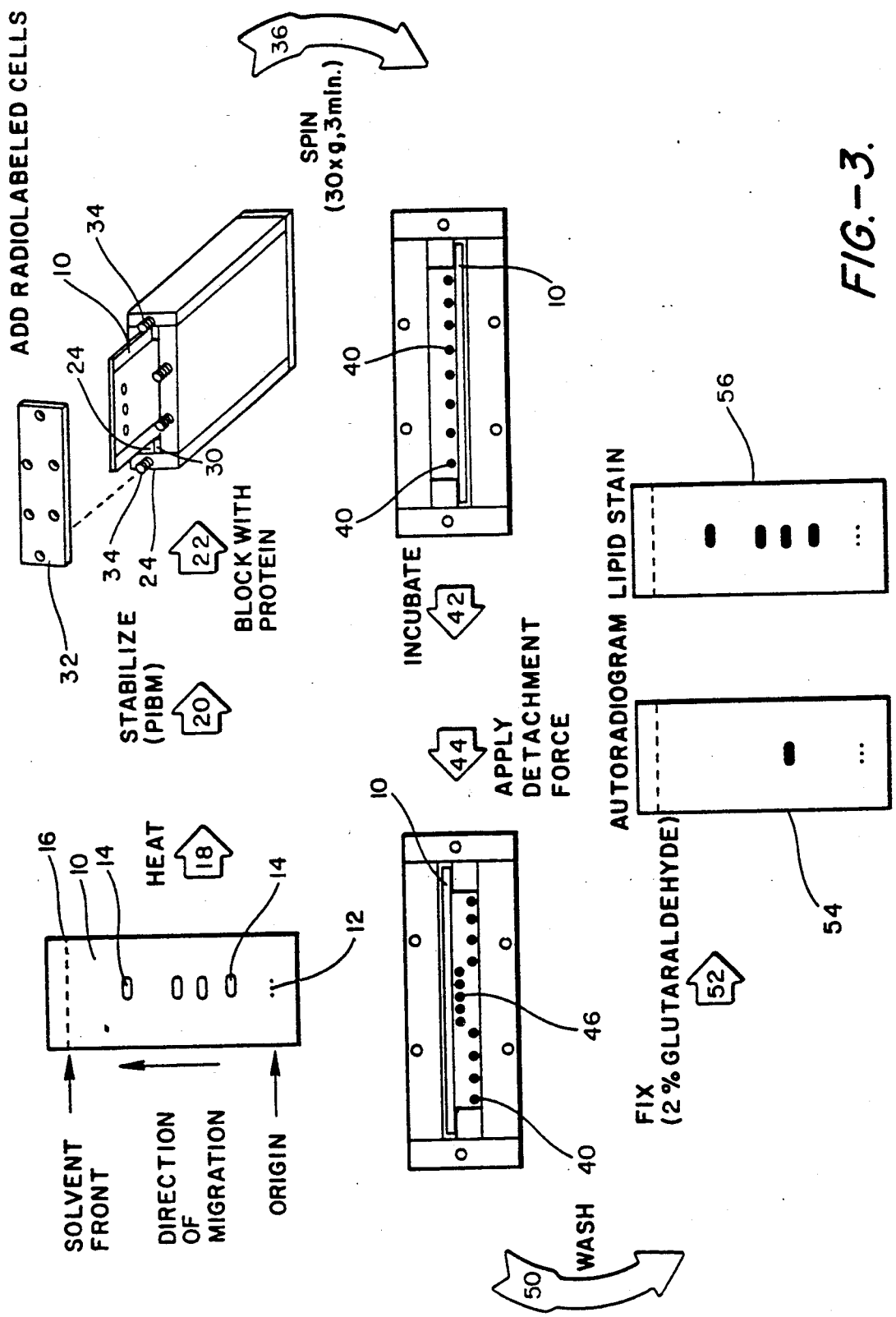
FIG. 3 is a schematic flow diagram of a process according to the subject invention.

In order to discuss the method, FIG. 3 will now be considered. A sample which contains the mixture to be separated, for example a mixture of glycosphingolipids, ceramides, glucosaminides, sialic acid glycoside, galactosaminide, mannose-6-phosphate glycosides, combinations thereof, or other complex carbohydrates or glycans is separated by conventional means on a thin layer chromatographic plate 10. The plate may have any adsorbent, such as silica, alumina, cellulose, or the like, but is preferably silica. The particular size of the plate is not critical to this invention, any size plate may be employed. However, for convenience, the dimensions of the plate will usually not exceed 20 cm along any edge, preferably not exceed about 10 cm. The amount of material separated on the plate may be varied widely, for the most part one will be concerned with very low concentrations of ligands. Thus, amounts as low as 0.01 nmol may be employed, usually at least about 0.2 nmol and 10 nmol or more may be employed. The particular amount will depend upon the nature of the composition, its complexity, the number of constituents in the composition, and the like.

Desirably, prior to use, the plate is heated at an elevated temperature to remove any adsorbed moisture, cooled, and pre-run in developing solvent. The developing solvent is removed by evaporation, the plate cooled and the sample applied adjacent one end of the chromatogram at the origin 12. The chromatograms may then be developed in accordance with conventional ways.

For glycosphingolipids, solvent systems which are found to be useful are combinations of chloroform and methanol, with the optional addition of 0.1-10% by volume aqueous potassium chloride (0.1-1% KCl) or water. Illustrative solvent systems include chloroform:methanol, 6:1; chloroform:methanol 3:1; chloroform:methanol:0.25% aqueous KCl, 60:35:8; or chloroform:methanol:water, 6:4:1. After development of the plates, the different components will migrate and the development will stop when the solvent front 16 approaches the opposite end of the chromatogram. The various components will be distributed as bands 14. The plates are then dried at an elevated temperature 18, allowed to cool briefly, and then dipped in an inert volatile organic solvent, a hydrophobic solvent, usually a hydrocarbon solvent, e.g. hexane or cyclohexane, followed by dipping in a solution of an appropriate polar polymer 20, such as an acrylate, particularly a methacrylate, more particularly a methacrylate having an ester group of from 2-6, usually about 4 carbon atoms.

In using polyisobutyl methacrylate it is found that the concentration and time of immersion should be optimized in each case. The polymer concentration will generally range from about 1-100 µg/ml, conveniently being prepared at the time of use from a more concentrated stock solution. The plate is thus stabilized by a short dip in a fresh polymeric solution 20.

At step 22, the plate may be blocked with protein to diminish non-specific binding of cells to the chromatogram. The plates are first preincubated in medium for a brief period, generally under 5 min, usually under 3 min. This is followed by incubation with an inert protein-containing solution, e.g. serum albumin, fibrinogen, or the like. The incubation will generally be for about 5-30 min, more usually about 10-20 min. The chromatogram is then incubated in a protein-free medium for an additional period of time within about the same previous time range. Desirably, the sides of the plates are stripped of adsorbent, if not done earlier, to allow for easy insertion into the holding container and physical restraint of the air bubbles, the chromatogram may now be introduced the chamber 24 of container 26. The chromatogram is slid into chamber 24 so as to be held firmly in place against the wall of container 26 by blocks 30. Once the chromatogram 10 is firmly placed in position, the cell containing medium is introduced into compartment 24. Desirably, the container 26 is prechilled prior to introduction of the chromatogram 10. The cell suspension is added to fill the chamber, the chamber being actually over-filled and sealed, taking care to avoid introduction of any bubbles. The cover 32 is fitted onto lug posts 34 and sealed with nuts not shown.

The container 26 is designed to fit into a 96-well plate centrifuge carrier and is then centrifuged under a low gravitational force, generally less than about 100g, preferably less than about 50g and at least about 15g for from about 1-5 min in step 36. As a result, the container now has cells 40 adhering to chromatogram 10, both specifically and non-specifically. The container is then heated, conveniently in a water bath, at about 25°-40° C., preferably about 37° C. and incubated for from 10-60 min in step 42. This step allows the cells to adhere specifically to the surface. The container 26 is then removed from the water bath, inverted, so that the bottom is placed upward in the centrifuge carrier and centrifuged at a reduced temperature at a moderately higher gravitational force than previously in step 44, generally greater than 250g and less than about 1000g. One now observes specifically bound cells 46 located in relation to a particular ligand while the remaining non-specifically bound cells 40 have moved away from chromatogram 10.

While still inverted, container 26 is immersed in an ice cold vat of buffer, cover 32 removed and the chromatogram plate 10 gently removed from chamber 24. : After righting the chromatogram plate 10, the plate is placed in a shallow dish which is also fully immersed and then the shallow dish or vessel may be further transferred to additional sources of fresh buffer without ever subjecting the plate to an air/liquid interface. Finally, the plate is transferred to a deeper dish where it is overlaid with fixation buffer, so as to fix the cells in position. Before detecting the cells, the cells are fixed with an appropriate cross-linking agent, e.g. glutaraldehyde in step 52. Any convenient fixing buffer may be employed. After sufficient time for fixing, the plate may then be repeatedly washed while still retained in the transfer dish and then dried. After drying, the presence of the lipid and presence of the cells may be determined in accordance with conventional ways.

For determining the presence of the cells, the cells can be made radioactive by incubation with a radioactive nutrient which becomes incorporated in the cell. Alternatively, various antibodies may be employed which bind to the cells and are labeled with enzymes or fluorescers, where the enzymes provide for a colored or fluorescent product. The particular manner in which the cells are detected is not critical to this invention and any useful method may be employed.

The lipid may be detected employing a variety of stains, conveniently Coomassie blue or other convenient oil stains. The chromatogram is now ready to be used to provide for an autoradiogram 54 and a lipid stained chromatogram 56.

Figure 1:
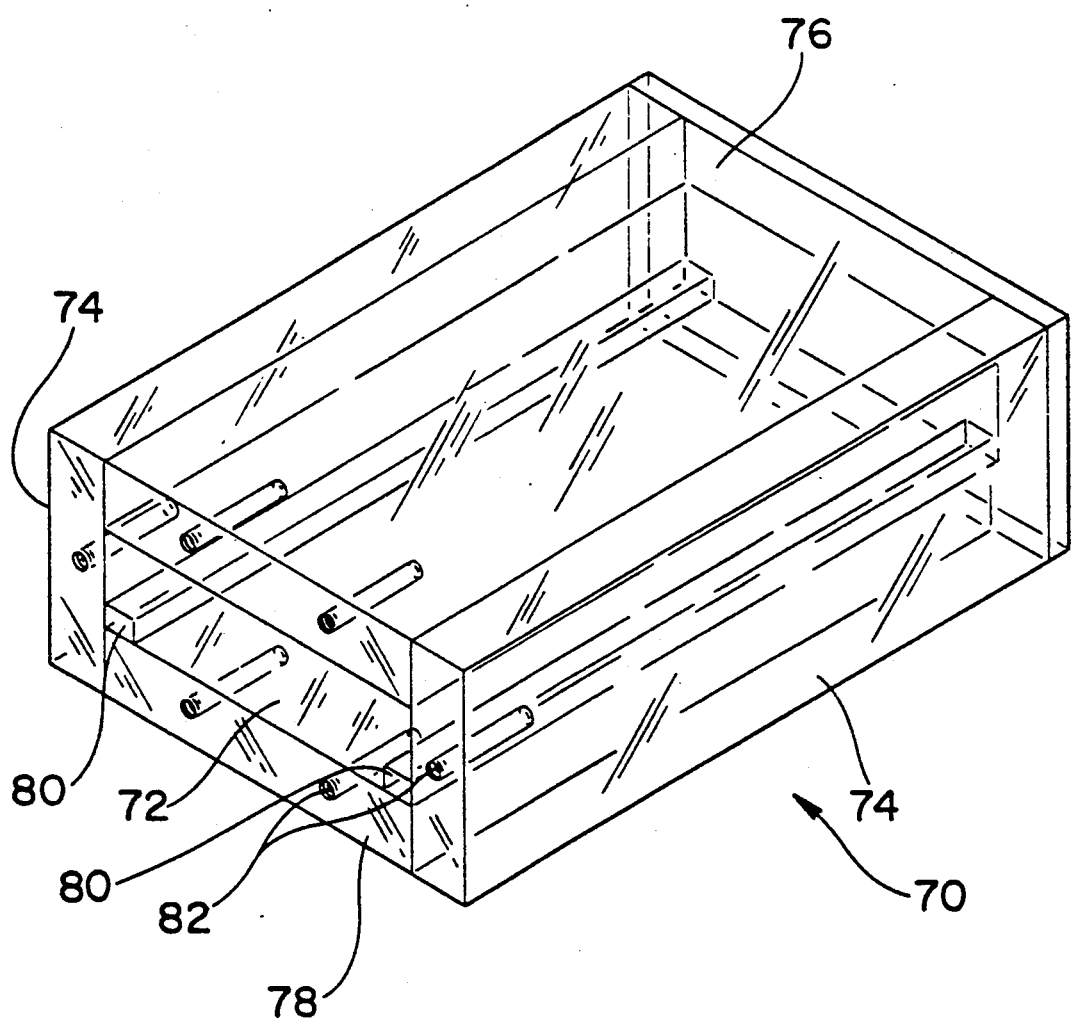
FIG. 1 is a perspective view of a containment box with one end opened.
Figure 2:
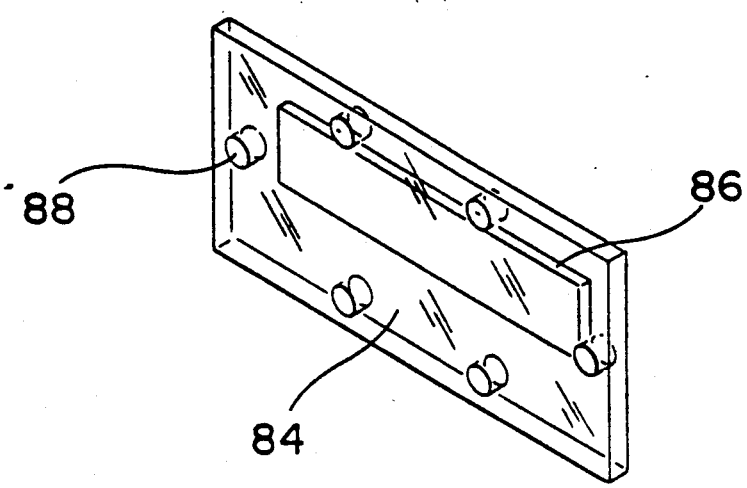
FIG. 2 is a gasket and cover for sealing the containment box of FIG. 1.

FIGS. 1 and 2 may now be considered in greater detail for the containment chamber or container. The container 70 is conveniently made of a non-adherent plastic, which is transparent so that one can observe events occurring within the container chamber 72. The container has sidewalls 74, ceiling or upper wall 76 and floor or lower wall 78. Blocks 80 serve to align and position the chromatogram adjacent to upper wall 76, with the chromatographic surface facing lower wall 78. For centrifugation it is of about 2.75 inches and a length about 4 inches with an inner width of about 2 1/32 inches. The wall thickness will generally be about ⅛ inch, with the height of the container being about 15/16 inch and the chamber being about 3/16 inch high. The chamber will have a volume of from about 20–25 ml. A plurality of threaded openings 82 are provided for receiving lug bolts which are not shown.

After introducing the chromatogram into the chamber 72, and filling the chamber with the cell-containing medium, the cell chamber is then sealed with cover 84. To provide a hermetic seal, gasket 86 covers the chamber 72 opening, extending beyond the opening of chamber 72. A plurality of non-threaded channels 88 are provided which mate with threaded openings 82 for receiving the lug bolts which pass through channels 88 and are threaded into threaded openings 82. Cover 84 is of a size to fit in conformance with container 70, so that the edges of cover 84 do not extend beyond the walls of cover 70.

For further understanding of the invention, the following examples will now be considered. The examples are offered by way of illustration and not the way of limitation.

EXPERIMENTAL

Binding of chicken hepatocytes was studied as follows. Chicken hepatocytes were prepared by collagenase profusion of juvenile chicken livers (Brandley and Schnaar, *J. Biol. Chem.* (1985) 260:12474–12483). Viable cells were separated from non-viable cells by a Percoll centrifugation procedure (Kreamer et al., *In Vitro Cell. Dev. Biol.* (1986) 22:201–211). After the cells were washed free of calcium by centrifugation in an EDTA-containing buffer, they were resuspended at a concentration of $10^7$ cells/ml in H-DMEM (Hepes-buffered Dulbecco's modified Eagles medium) containing 2 mg/ml Bovine Serum Albumin (BSA). 20 ml of cell suspension was added to 19.2 ml of a Percoll stock solution prepared by mixing 9 parts Percoll (Pharmacia, Inc.) with 1 part 10-fold concentrated calcium-magnesium-free PBS. The cell suspension/Percoll mixture was agitated gently and centrifuged at 190g for 10 min, and the cell pellet resuspended in 10 ml of PF-MEM (Phosphate-Free Minimum Essential Medium) and collected by centrifugation (150g, 3 min). The final cell pellet was suspended at a concentration of $5 \times 10^6$ cells/ml in PF-MEM supplemented with 5 mg/ml BSA. The resulting population contained >90% viable cells. An aliquot of cell suspension (15 ml) and $^{32}P$ (0.25 mCi) were placed in a 125-ml Erlenmeyer flask in a rotating water bath under nonaggregating conditions (125 rpm, 37° C.) for 60–90 min. The radiolabeled cells were collected by centrifugation (150g, 3 min), washed three times by centrifugation in 10 ml of H-DMEM, resuspended at a concentration of $5-8 \times 10^5$ cell/ml in H-DMEM supplemented with 50 mg/ml BSA, and kept at 0° C. until use (within 4 h). Cells averaged >1 dpm $^{32}P$/cell, and >98% of the radiolabel remained cell-associated at the time of the experiment.

Commercially obtained prescored 10 × 10-cm HPTLC plates were reduced in size to 5 × 5 cm, and a 0.5-cm strip of silica was scraped from each of two opposite edges of each plate (in the direction of chromatographic development) to allow easy insertion into the plate chamber. The plates were heated at 120° C. for 10 min, cooled, prerun in developing solvent, reheated as above and cooled, and glycolipids were applied in 5-mm lanes 1 cm from the bottom of the plate. Chromatograms were developed in Solvent A (chloroform: methanol, 6:1), Solvent B (chloroform: methanol, 3:1), Solvent C (chloroform:methanol:0.25% aqueous KCl, 60:35:8), or Solvent D (chloroform: methanol:water, 6:4:1) and then dried thoroughly (50° C., 1 h). The dried plates were allowed to cool briefly, dipped sequentially (for 30 sec each) in hexane and hexane-containing a varied concentration level of poly(isobutylmethacrylate) (PIBM), and then allowed to dry for 2 h at ambient temperature. The PIBM/hexane solution, ranged in concentration up to 65 µg/ml and was prepared by adding 5g PIBM to rapidly stirring chloroform (50 ml) and allowed to fully dissolve (30 min). An aliquot of this stock solution (0.5 ml) was diluted into 1000-fold that volume of rapidly stirring hexane. After stirring for 1 h, an aliquot of the hexane solution (20 ml) was removed to a tared flask, the solvent evaporated, and the concentration of polymer (approximately 100 µg/ml) determined. The final working solution of PIBM ranged from 1–65 µg/ml in hexane. Fresh solution was prepared before use for each plate and then discarded.

PIBM-coated chromatograms were preincubated in medium prior to insertion into the adhesion chamber. The thoroughly dried chromatograms were immersed in H-DMEM for 1 min, then in the same medium containing 50 mg/ml BSA for 15 min, and finally H-DMEM (without BSA) for 15–30 min. The presoaked plates were dipped briefly in fresh H-DMEM to dislodge any air bubbles attached to to the silica gel surface and then inserted (silica-coated surface toward the top of the chamber) into the prechilled chamber. Cell suspension was then added to fill the chamber (approximately 18 ml) and the chamber overfilled with medium and sealed, taking care to avoid introduction of any air bubbles. The chamber was gently agitated, placed top upward in a 96-well plate centrifuge carrier and centrifuged (30g, 3 min, 4° C.) to ensure that the cells came into contact evenly with the TLC plate surface. After centrifugation, the the chamber was immersed (top upward) in a 37° C. water bath and incubated for 30 min to allow adhesion to occur. The chamber was removed from the water bath, inverted, placed bottom upward in the centrifuge carrier, and centrifuged (550g, 10 min, 4° C.) to remove any nonadherent cells from the TLC plate surface. While still inverted, the chamber was fully immersed in an ice-cold vat of PBS, the cover removed and the TLC plate gently removed and righted (silica-coated side now upward) and placed in a shallow (55 × 105 × 6 mm) plexiglass dish, which was also fully immersed. In this way, the TLC plate is washed by transferring it to a fresh source of PBS without ever drawing it through an air/liquid interface. After one additional PBS wash, the TLC plate, still in the transfer dish, was placed in the bottom of a deeper dish (150-cm² tissue culture flasks with one side removed were found to be convenient) and overlaid (gently) with 100–150 ml of fixation buffer (13 parts PBS, 11 parts water and 1 part 50% glutaraldehyde solution). After 30 min at ambient temperature, the TLC plate, still in the transfer dish, was washed three times by immersion in PBS, removed from the transfer dish with forceps and placed in a vertical position to dry. The dry plate was placed on preflashed or non-preflashed (depending upon the experiment) Kodak X-Omat AR X-ray film and exposed at −70° C. in the presence or absence of an enhancing screen. After exposure for 30 min to 24 h, the plates were removed and the film processed per the manufacturer's instructions. Glycolipids (when present at >500 pmol/lane) were detected by incubating the TLC plates is Coomassie blue (0.3 mg/ml) in methanol:water (1:5) for 30 min followed by destaining in the same solvent mixture for 5 min.

Figure 4:
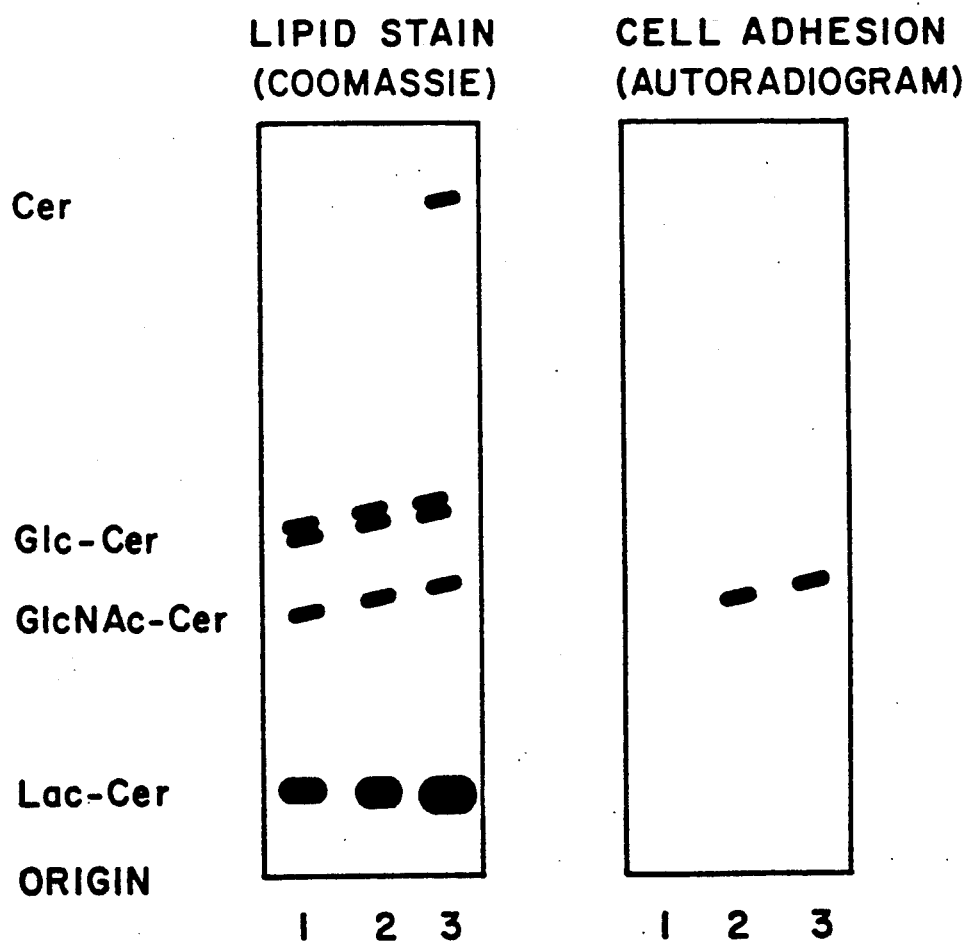
FIG. 4 shows the results of a lipid stain and cell adhesion autoradiogram developed in accordance with the subject invention.

The patterns of the two profiles resulting from autoradiography and from lipid staining were compared to determine the structural specificity of binding (see FIG. 4). The small amount of radiolabel at the origin (lane 2) is an artifact due to cell binding to the underlying glass plate uncovered during sample application or handling. The bands clearly demonstrate that the chicken hepatocytes preferentially bind to the GlcNAc-deoxyceramide.

In the next study, adhesion of 10-day embryonic chick (E10) neural retina cells directly to gangliosides resolved by thin-layer chromatography was investigated. Intact neural retinae were radiolabeled by incubation in phosphate-free Minimum Essential medium containing $^{32}P$ for 1 h at 37° C. The tissue was washed and incubated with trypsin (3X crystallized 0.1 mg/ml) and DNase (0.08 mg/ml) in calcium- and magnesium-free phosphate buffered saline for 15 min at 37° C. After inactivation of the trypsin by the addition of trypsin inhibitor (0.5 mg/ml) and chilling of the suspension, the tissue was dissociated by trituration. After washing the cell suspension, $5 \times 10^7$ to $1 \times 10^8$ cells were recovered per retina The cells were found to be 90-95% viable and 75-85% exist as single cells. Radiolabeling efficiency was 0.03-0.1 cpm/cell of which 75-85% remains cell-associated after experimental incubations.

Adhesion to three gangliosides ($G_{T1b}$, $G_{D1a}$, and $G_{M1}$) and the control lipids globoside and sulfatide were investigated. An aliquot of a mixture containing 1000, 750, 500, 250, 200, 100, or 50 pmols of each lipid was applied to a $5 \times 10$-cm HPTLC plate and developed in chloroform:methanol:water (6:4:1). After the chromatogram was heated at 50° C. and allowed to cool, it was dipped sequentially (for 30 sec each) in hexane and hexane-containing PIBM (2 μg/ml). The dried chromatogram was presoaked in medium (H-DMEM for 1 min; in the same medium containing 70 μg/ml fibrinogen for 15 min; and finally in H-DMEM without fibrinogen for 45-60 min). The TLC plate was then inserted into the chamber and exposed to radiolabeled neural retina cells at a density equivalent to $4 \times 10^5$ cells/cm$^2$ as described previously. The results demonstrated binding to the 3 gangliosides, with no binding to the sulfatide or globoside, with some preference for $G_{T1b}$.

It is evident from the above results that a convenient, efficient and rapid procedure is provided for determining the binding propensities of cells for carbohydrates. The apparatus is simple and can be readily fabricated in a laboratory, can be used in a reproducible manner with mammalian cells, and can demonstrate varying levels of binding between different carbohydrates.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. An apparatus for binding cells to a thin layer chromatogram surface, said apparatus comprising:
   (a) a sealable chamber suitable for fitting into a multiwell plate centrifuge carrier, said chamber having a side opening for receiving a thin layer chromatogram;
   (b) blocks adjacent the floor of said chamber and along the sides of said chamber to hold said chromatogram against the ceiling of said chamber;
   (c) gasket means and a cover cooperating to provide an air-tight seal for said opening; and
   (d) means for locking said cover into a sealing position with respect to said opening;
   wherein said locking means and said seal are capable of withstanding centrifugal forces in the range of approximately 250 to 1000 times the force of gravity.

2. An apparatus according to claim 1, wherein said chamber is constructed of clear non-adherent plastic.

3. An apparatus according to claim 1, further comprising a thin layer chromatogram.

4. An apparatus according to claim 1, having an inner volume of from about 20 to 25 ml.

5. An apparatus for binding cells to a thin layer chromatogram surface as set forth in claim 1, wherein the locking means includes at least one post and at least one fastener, the post and the fastener cooperating to apply compressive forces to the cover and the chamber, thereby locking the cover into a sealing position.

6. An apparatus for binding cells to a thin layer chromatogram surface as set forth in claim 1, wherein said side opening is adapted to receive a cell suspension, and said gasket means, said cover, and said chamber cooperate to retain the cell suspension when the cover is locked into the sealing position.

* * * * *